(12) United States Patent
Foerger et al.

(10) Patent No.: US 9,101,703 B2
(45) Date of Patent: Aug. 11, 2015

(54) MEDICAL APPLIANCE

(75) Inventors: Jens Foerger, Laubuseschbach (DE);
Stefan Oesterreich, Neu-Anspach (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 411 days.

(21) Appl. No.: 13/361,015

(22) Filed: Jan. 30, 2012

(65) Prior Publication Data
US 2012/0200214 A1    Aug. 9, 2012

Related U.S. Application Data

(60) Provisional application No. 61/457,220, filed on Feb. 3, 2011.

(30) Foreign Application Priority Data

Feb. 3, 2011   (DE) .......................... 10 2011 010 249

(51) Int. Cl.
| | | |
|---|---|---|
| *E05C 3/02* | (2006.01) | |
| *A61M 1/14* | (2006.01) | |
| *E05B 15/02* | (2006.01) | |
| *E05C 3/04* | (2006.01) | |
| *E05B 15/10* | (2006.01) | |
| *E05C 3/00* | (2006.01) | |

(52) U.S. Cl.
CPC .............. *A61M 1/14* (2013.01); *E05B 15/0245* (2013.01); *E05B 15/101* (2013.01); *E05C 3/045* (2013.01); *E05C 3/046* (2013.01); *A61M 2209/08* (2013.01)

(58) Field of Classification Search
CPC ... E05B 15/101; E05B 15/0245; E05C 3/045; E05C 3/046
USPC ........ 292/95, 96, 177–182, 240, 241, 256.69, 292/341.15, DIG. 49
See application file for complete search history.

(56) References Cited

U.S. PATENT DOCUMENTS

| | | | | |
|---|---|---|---|---|
| 111,524 | A * | 2/1871 | Drott .............................. | 292/182 |
| 390,507 | A * | 10/1888 | Morton .......................... | 292/179 |
| 966,926 | A * | 8/1910 | Knapp ............................. | 16/70 |
| 1,216,414 | A * | 2/1917 | Calkins .......................... | 292/111 |
| 1,250,574 | A * | 12/1917 | Ferris ............................ | 292/113 |
| 1,358,885 | A * | 11/1920 | Shimocuskies ................. | 70/150 |
| 1,601,359 | A * | 9/1926 | Harrington ..................... | 70/100 |
| 1,661,548 | A * | 3/1928 | Stuart et al. ................... | 292/127 |
| 1,937,978 | A * | 12/1933 | Miller ........................... | 292/127 |
| 2,340,864 | A * | 2/1944 | Carpenter ..................... | 52/127.9 |

(Continued)

FOREIGN PATENT DOCUMENTS

| | | |
|---|---|---|
| DE | 693 00 856 | 4/1996 |
| DE | 3900814 C2 * | 3/1997 |
| DE | 102008008704 A1 * | 8/2009 |

*Primary Examiner* — Carlos Lugo
(74) *Attorney, Agent, or Firm* — Jacobson Holman, PLLC

(57) ABSTRACT

A medical appliance, in particular an apparatus for extracorporeal blood treatment, has a housing including a door and with a handle mechanism arranged at the door, via which the door can be locked with the housing via a locking mechanism. A part of the locking mechanism is formed at the handle mechanism in a part thereof that protrudes into the housing. A form-fit unit includes at least one form-fit element and at least one form-fit element counterpart, such that on locking and/or closing the door, the at least one form-fit element at least partly engages in the at least one form-fit element counterpart.

23 Claims, 3 Drawing Sheets

(56) References Cited

U.S. PATENT DOCUMENTS

| | | | |
|---|---|---|---|
| 2,446,113 A * | 7/1948 | Spiller | 292/30 |
| 2,496,087 A * | 1/1950 | Fleming | 244/2 |
| 2,647,287 A * | 8/1953 | Jones | 52/582.2 |
| 2,704,218 A * | 3/1955 | Claud-Mantle | 292/113 |
| 2,706,316 A * | 4/1955 | Jones et al. | 52/582.2 |
| 2,706,317 A * | 4/1955 | Whittlesey | 52/582.2 |
| 2,714,751 A * | 8/1955 | Stuart et al. | 52/582.2 |
| 2,775,799 A * | 1/1957 | Gerhard | 52/582.2 |
| 2,828,991 A * | 4/1958 | Stilger | 292/175 |
| 2,944,864 A * | 7/1960 | Krivulka | 312/332.1 |
| 2,964,808 A * | 12/1960 | Kloess, Jr. | 49/213 |
| 3,560,038 A * | 2/1971 | Gunther | 92/241 |
| 4,006,121 A * | 2/1977 | Isono | 200/61.64 |
| 4,179,143 A * | 12/1979 | Shy | 292/179 |
| 4,348,036 A * | 9/1982 | Settembre | 280/615 |
| 4,417,430 A * | 11/1983 | Loikitz | 52/582.2 |
| 4,776,620 A * | 10/1988 | Marks et al. | 292/228 |
| 5,120,096 A * | 6/1992 | D'Silva | 292/241 |
| 5,127,684 A * | 7/1992 | Klotz et al. | 292/113 |
| 5,174,618 A * | 12/1992 | Kropf | 292/254 |
| 5,452,925 A * | 9/1995 | Huang | 292/57 |
| 5,484,176 A * | 1/1996 | Sallwasser | 292/137 |
| 5,746,456 A * | 5/1998 | Violi et al. | 292/146 |
| 5,988,709 A * | 11/1999 | Lee et al. | 292/199 |
| 6,527,315 B2 * | 3/2003 | Marks et al. | 292/341.15 |
| 7,347,460 B2 * | 3/2008 | Ala | 292/216 |
| 7,819,441 B1 * | 10/2010 | Coman et al. | 292/251.5 |
| 7,866,712 B2 * | 1/2011 | Kintz | 292/121 |
| 7,871,113 B2 * | 1/2011 | Watanabe et al. | 292/336.3 |
| 7,976,078 B2 * | 7/2011 | Steinbeck et al. | 292/194 |
| 8,113,551 B2 * | 2/2012 | Baic et al. | 292/113 |
| 8,651,535 B2 * | 2/2014 | Oppel et al. | 292/198 |

* cited by examiner

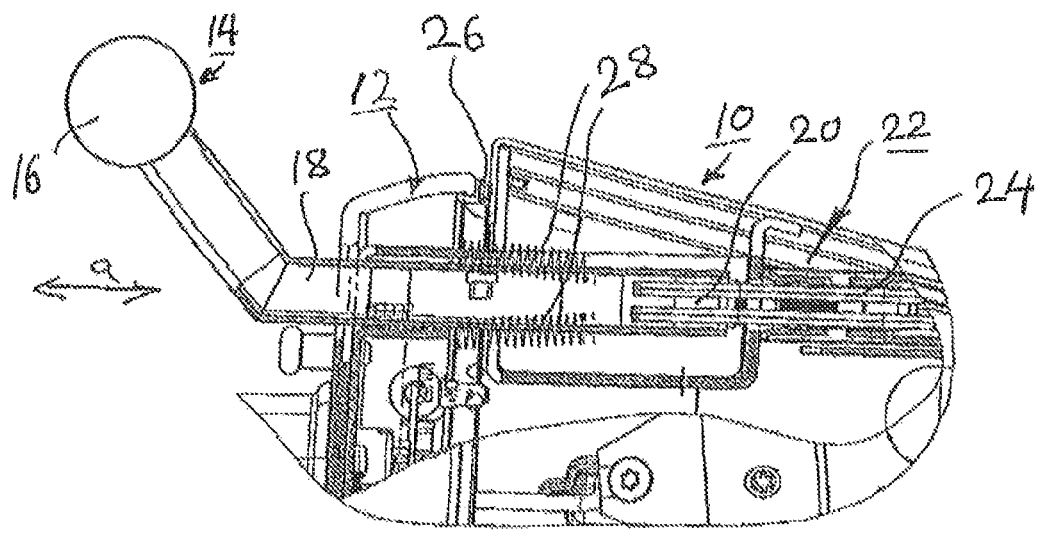
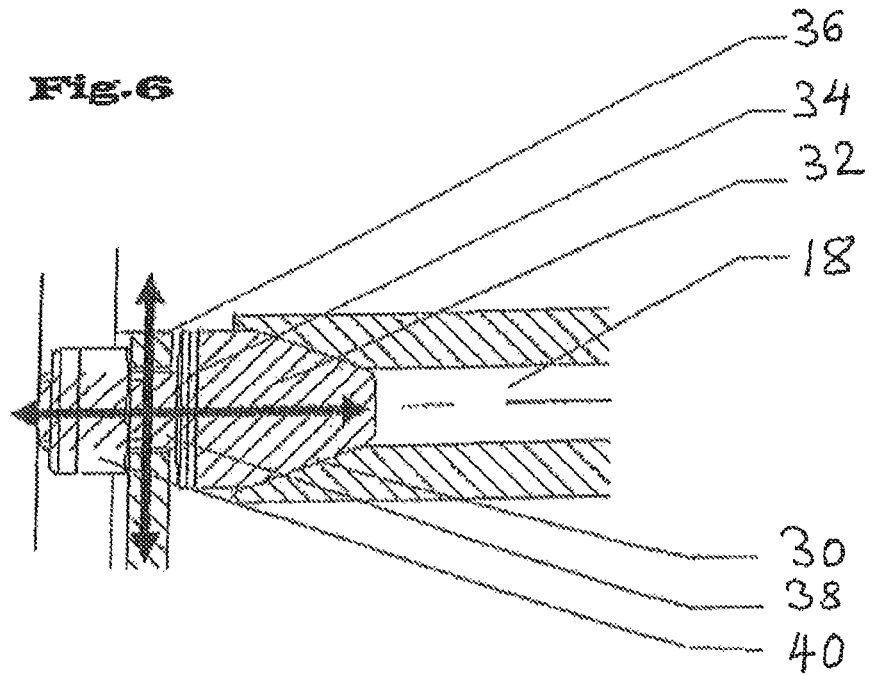

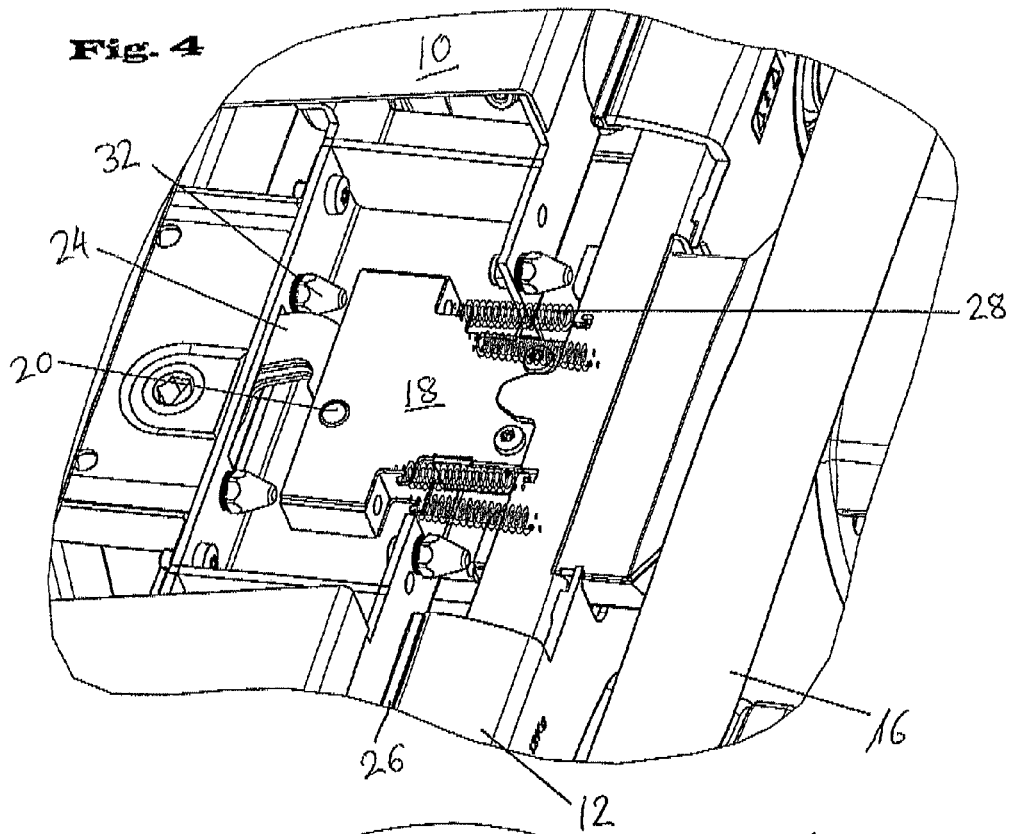
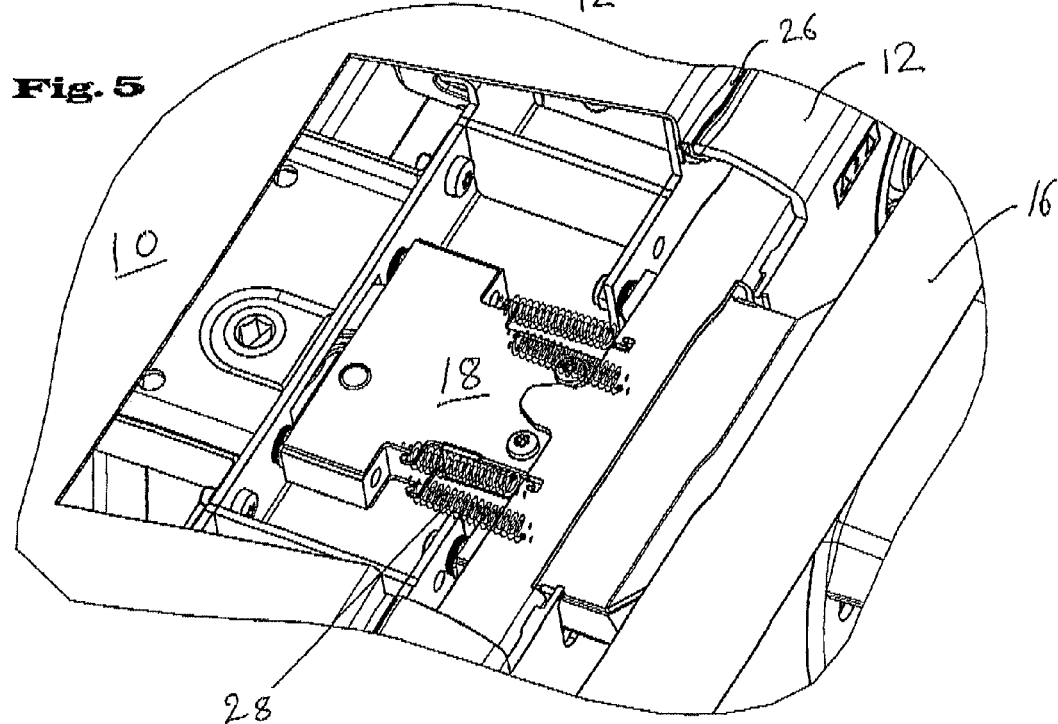

MEDICAL APPLIANCE

CROSS-REFERENCE TO RELATED APPLICATIONS

This application claims benefit of U.S. provisional application No 61,457,220, filed Feb. 3, 2011, and the priority of German number 10 2011 010 249.3 filed Feb. 3, 2011, hereby incorporated by reference.

BACKGROUND OF THE INVENTION

1. Field of Invention

This invention relates to a medical appliance, in particular an apparatus for the extracorporeal blood treatment, having a housing including a door, and with a handle mechanism arranged at the door, via which the door can be locked with the housing via a locking mechanism.

2. Description of the Prior Art

Medical appliances, such as apparatuses for the extracorporeal blood treatment, usually have a housing which for cost reasons very often is made of a simple sheet-metal construction. The housing might also be a supporting plastic construction. In particular, it is conceivable that the housing includes a supporting sheet metal construction which is framed with plastic parts. In the housing at least one door generally is provided, which leaves an inspection opening for the service technician. Usually, a corresponding handle for opening the door is arranged at the door.

Apparatuses for the extracorporeal blood treatment are known as so-called acute dialysis machines, which serve for use in intensive care units and for this purpose are designed to be movable on rollers. To move such acute dialysis machine with a weight of approximately 85 kg, the same usually is held by the door handle.

Thus, the door handle has a dual function. On the one hand, it serves the service technician for opening and closing the door and on the other hand it serves the user of the dialysis machine in the hospital as a handle for pushing the entire dialysis machine. While pushing the machine, forces are transmitted from the handle mechanism to the housing.

In some cases of use, the door constitutes the entire housing front and is provided with a circumferential elastic seal which on closing is pressed against the frame of the stationary housing. In doing so, the seal should not be pressed against the frame either too strongly or too weakly. In addition, manufacturing tolerances must be compensated, which are inevitable due to the use of the canted inexpensive sheet-metal construction.

Despite these manufacturing tolerances, the door on the one hand should circumferentially abut in a sealing manner without distortion and on the other hand the handle should not have a noticeable clearance on pushing the dialysis machine. When using known door handles, the seal is deformed in addition when pushing the dialysis machine. The fact that the handle noticeably yields while being pushed by the user provides the entire dialysis machine with a negative quality impression, which should be avoided.

SUMMARY OF THE INVENTION

Accordingly, it is the object of the present invention to provide a medical appliance which includes a door handle which despite a simple construction should feel massive and should not yield on pushing the medical appliance. At the same time it should be possible to open and close the door of the medical appliance via the handle.

In accordance with the invention, this object is solved by a medical appliance having the features described herein. Accordingly, the medical appliance has a housing comprising a door and a handle mechanism. arranged at the door, by means of which the door can he locked with the housing via a locking mechanism. At the handle mechanism a part of the locking mechanism is formed in its part protruding into the housing, which cooperates with the other part of the locking mechanism on the side of the housing. It is provided that at the handle mechanism, in its part protruding into the housing, a part of the locking mechanism is formed and that at least one form-fit unit is provided which includes at least one form-fit means and at least one form-fit means counterpart, wherein on locking and/or closing the door that at least one form-fit means at least partly engages in the at least one form-fit means counterpart.

This involves the advantage that a defined positioning of the door with respect to the housing can be achieved. In particular it is advantageous that correct closing thereby can be ensured in a safe and simple way, with a simple construction being possible at the same time.

The housing can be fabricated of a simple sheet-metal construction. The housing might also be a supporting plastic construction. Advantageously, it is conceivable in particular that the housing includes a supporting sheet metal construction which is framed with plastic parts. In an advantageous aspect, the medical appliance can be a dialysis machine, e.g. an acute dialysis machine.

Advantageous aspects of the invention are described in the followinq detailed description.

It can be provided that at least one form-fit means and/or at least one form-fit means counterpart is arranged at and/or integrally molded and/or attached to the handle mechanism.

It is furthermore conceivable that at least one form-fit means and/or at least one form-fit means counterpart is arranged and/or integrally molded and/or attached on the side of the housing.

In particular, it is advantageously possible that on the side of the housing and on the side of the handle mechanism both at least one form-fit means and at least one form-fit means counterpart are provided. Just as well it is, however, also possible that on the side of the housing the form-fit means is provided and on the side of the handle mechanism the form-fit means counterpart is provided. As a further equally advantageous possibility it is, however, also conceivable that on the side of the handle mechanism the form-fit means is provided and on the side of the housing the form-fit means counterpart is provided.

In addition, it can be provided that the at least one form-fit means and/or at least one form-fit means counterpart is elastically mounted.

It is furthermore possible that the form-fit unit includes a tapered spigot as form-fit means and a conical receptacle as form-fit means counterpart.

It is conceivable that on closing the handle mechanism engages in at least one tapered spigot elastically mounted on the side of the housing via at least one conical receptacle and/or that on closing the handle mechanism engages in at least one conical receptacle on the side of the housing via at least one tapered spigot elastically mounted on the side of the handle mechanism. On closing the door by means of the locking mechanism, the at least one conical receptacle thus advantageously is pretensioned into the at least one tapered spigot elastically mounted on the side of the housing and/or on the side of the handle mechanism such that on pushing the medical appliance the usual thrust forces received by the handle can be transmitted to the housing, without the handle being displaced with respect to the housing. At the same time, the at least one elastically mounted tapered spigot advantageously can compensate the manufacturing tolerances in all directions.

It is furthermore possible that at least one spring means is provided, by means of which the at least one form-fit means can be pretensioned.

Advantageously it can be provided that the spring means is and/or comprises a compression spring, a coil spring and/or a disk spring and/or that the spring means is at least partly formed by elastic regions of the housing.

It is in particular conceivable that the at least one tapered spigot is pretensioned via at least one disk spring. By using the disk springs, the tapered spigots advantageously can elastically be mounted on the housing, more exactly on the housing frame, in a three-dimensional way.

The disk springs can be pretensioned by a desired amount, in order to nevertheless provide for a sufficiently rigid transmission of force from the handle to the housing after closing the door and elastically compensating possible tolerances.

In accordance with a further preferred aspect of the invention a plurality of tapered spigots are arranged in the housing in at least two planes. Preferably, four tapered spigots are present here in two different planes of the housing frames. An alternative configuration can, however, also consist in that in one plane two tapered spigots are present and in a second plane a single tapered spigot is present.

The locking mechanism can include a pivotable hook which cooperates with a tension bolt in a known way for locking and unlocking the door. The pivotable hook can be provided with a latch in the usual way, by means of which the locking mechanism can be opened.

In accordance with one configuration variant the handle mechanism is firmly connected with the door. In another configuration variant the handle mechanism extends through the door in a longitudinally movable manner. In accordance with this configuration variant the handle mechanism includes at least one tension spring which can be tensioned on closing the door.

Due to the spring force of the at least one tension spring a defined compression of a seal arranged between the door and the housing, to be more exact the housing frame, is effected. In accordance with a further preferred aspect the pressing force is designed in dependence on the seal used. In so far, a uniform compression of the seal additionally is ensured by this configuration variant.

It is furthermore conceivable that at least a part of the housing front is formed as door.

In accordance with an advantageous configuration variant the entire housing front is formed as door. The door can be rotatably mounted about its lower edge, as is known for example from a baking oven door, whereas the handle mechanism is arranged on the opposite side of the door, i.e. close to the upper edge.

BRIEF DESCRIPTION OF THE DRAWINGS

Further features, details and advantages of the invention will be explained in detail with reference to an embodiment illustrated in the drawing, in which:

FIG. 1: shows a sectional representation through a part of the medical appliance in accordance with one configuration variant of the present invention, FIG. 4: shows a perspective, partly sectional representation of the medical appliance corresponding to FIG. 2 in an open position, FIG. 5: shows a representation according to FIG. 4 in a closed position, and FIG. 6: shows a detail section through another part of the medical appliance.

DETAILED DESCRIPTION OF THE PREFERRED EMBODIMENTS

Figure 2:
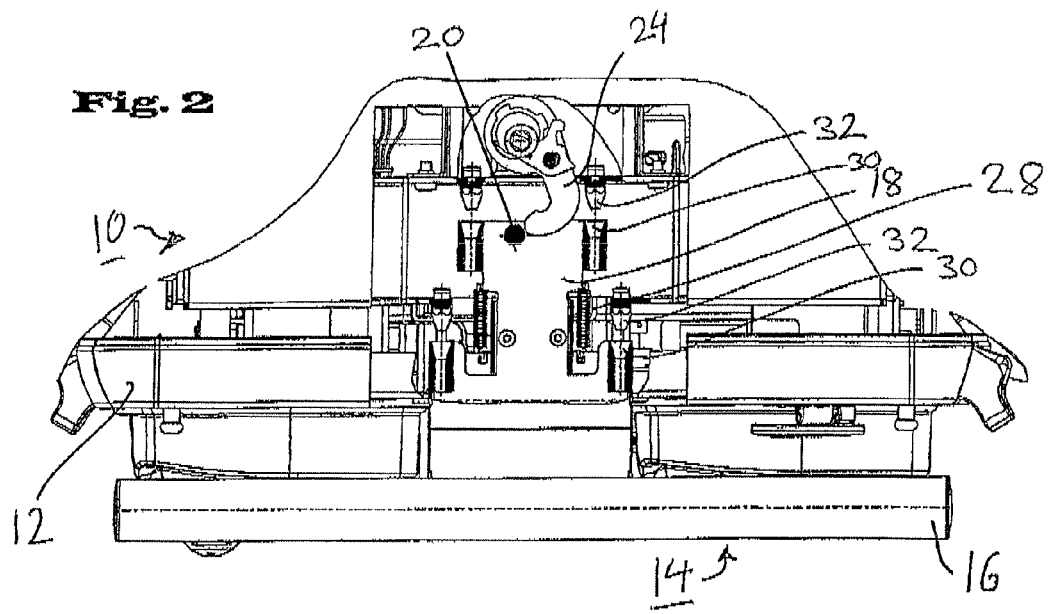
FIG. 2: shows a further sectional representation of the detail of FIG. 1 in an open position.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The Figures merely show the handle region or closure mechanism of a door 12 closing a housing of a non-illustrated medical appliance. The medical appliance advantageously, but not exclusively, can be an acute dialysis machine, which usually is mounted on rollers, so as to be able to move the same to the respective intensive care bed for use in an intensive care unit.

For this purpose, the entire device is seized by the handle 14. The handle 14 includes a handle bar 16 which is attached to the free end of a handle web 18 protruding from the door 12. The handle web 18 extends through the door 12 and is movably mounted in the same, as can be taken in particular from FIG. 1. In the handle web 18, a tension bolt 20 is inserted at the free end protruding into the housing 10, which is part of a locking means 22.

This locking means 22 substantially includes a pivotable hook 24 which cooperates with the tension bolt 20 and secures the door after correspondingly locking the tension bolt 20. The construction of the locking means 22 is of the conventional type and can be purchased as a toggle latch for a butt-joint lock. It provides for the hook 24 automatically snapping into the tension bolt on closing the door 12 and for a release of the tension bolt 20 by the hook 24 after correspondingly opening the door by a manipulation not shown here in detail.

Both the entire housing 10 and the door 12 are made of a canted sheet-metal construction. At the upper edge of the door 12 a circumferential seal 26 is provided, which is directed towards the housing 10.

The seal should rather uniformly rest against the canted supporting edge or frame of the housing 10.

To ensure a safe and completely closed contact of the seal 26 in the region between the door 12 and the housing 10, the handle 14 movably mounted in the door 12 in direction of the double arrow A as shown in FIG. 1 can be pretensioned via springs 28. For closing the door 12, the handle thus is pressed into the door against the spring force of the springs 28, until the hook 24 secures the tension bolt 20. The spring force of the springs 28 is chosen such that a rather uniform pressure is exerted on the door 12, so that the seal 26 reliably rests on the circumferential edge of the housing 10 and performs its sealing function.

In the embodiment shown here, four tension springs 28 are provided. Thus, on closing the door the door 12 first meets with the circumferential frame of the housing 10, while the handle 14 continues to move through the lead-through into its locking position and thereby tensions the tension springs 28. The pressing force of the tension springs should be designed for the defined pressing of the door with the housing frame, each in dependence on the seal used. For a medium-soft seal a pressing force between 150 and 200 N can be chosen. In this way, relatively large manufacturing tolerances which are due to the fabrication of the sheet-metal parts can be compensated.

From FIGS. 2, 3, 4 and 5 it can furthermore be taken that conical receptacles 30 are recessed at the handle web 18. On closing the door 12, the same cooperate with corresponding tapered spigots 32. In the embodiment shown here, the form-fit unit comprises the conical receptacles 30 and the corresponding tapered spigots 32. The form-fit means are formed by the tapered spigots 32 and the form-fit means counterparts are formed by the conical receptacles 30.

With reference to FIG. 6 the mode of action of the interlocking conical receptacles 30 and of the tapered spigot 32 can be explained. On its bottom surface the tapered spigot 32 includes a threaded bolt 38 via which it can be put through the frame 36 of the housing 10 and be fixed with a nut 40. On the opposite side of the frame 36, disk springs are pushed onto the threaded bolt 38, which can be pretensioned via the nut 40. As can furthermore be taken from FIG. 6, a sufficient radial clearance is present around the threaded bolt 38 in the bore extending through the frame 36. Due to the pretensioned disk springs via which the threaded bolt 38 supports on the frame 36 of the housing 10 and the radial clearance in the region of the bore, a three-dimensional elastic bearing is ensured, as is indicated by the movement arrows in FIG. 6.

Figure 3:
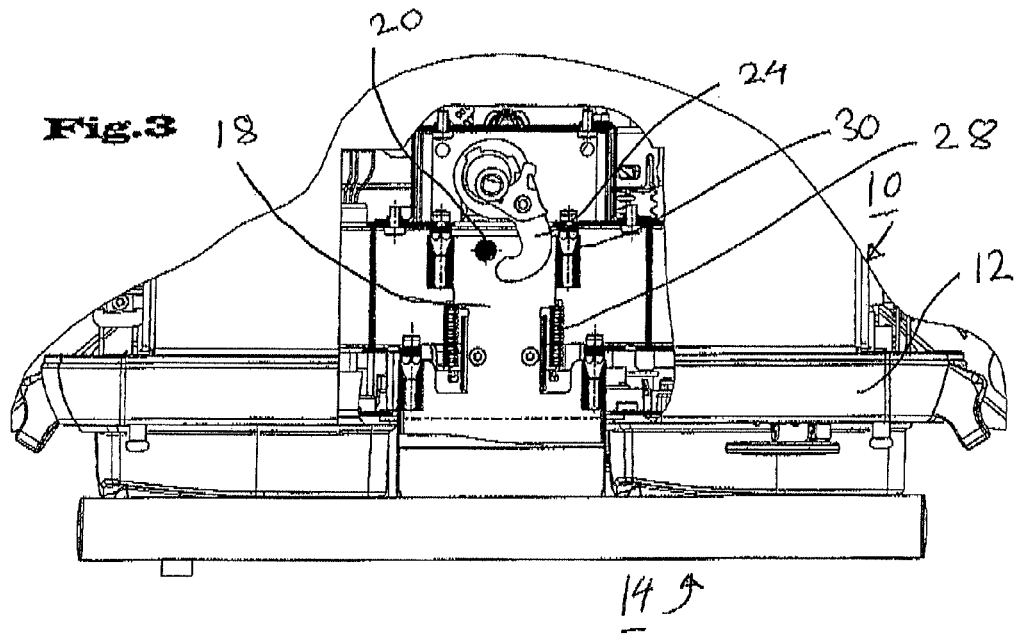
FIG. 3: shows the detail representation of the medical appliance of FIG. 2 in a closed, but not yet locked position.

As can now be taken from FIGS. 2, 3, 4 and 5, corresponding tapered spigots 32 and conical receptacles 30 are provided at several points of the housing 10 and/or of the handle 14. In this configuration variant two tapered spigots 32 are arranged in the set-back part of the housing, in which the hook 24 is rotatable mounted. As can clearly be seen in the Figures, the associated conical receptacles 30 are formed in the corresponding region of the handle web 18, wherein in FIGS. 2 and 4 the conical receptacles 30 do not yet sit on the tapered spigots 32. In FIGS. 3 and 5, on the other hand, the conical receptacles 30 are already coupled with the tapered spigots 32 elastically mounted on The side of the housing. Two tapered spigots 32 also are coupled with further conical receptacles 30 arranged at the handle web 18, which are arranged in the outer frame region of the housing 10 and hence are arranged in a different plane than the above-described tapered spigots 32.

The spring rigidity of the disk springs 34 used in the tapered bolts is designed such that the usual thrust forces on pushing the medical appliance, i.e. in the present example the dialysis machine, cannot lead to noticeable elastic deformations of the disk springs. This results in the haptic feeling of a "massive" and rigid handle 14 and a direct force transmission of the thrust forces to the medical appliance. Furthermore, the three-dimensionally elastically mounted tapered spigots 32 compensate the manufacturing tolerances in all directions. Beside the four tapered spigots 32 illustrated in this configuration variant one embodiment might also consist of only three or two tapered spigots which are arranged on two planes. Correspondingly dimensioned, an embodiment with a single tapered spigot also can already provide the effect in accordance with the invention.

The invention being thus described, it will be apparent that the same may be varied in many ways. Such variations are not to be regarded as a departure from the spirit and scope of the invention, and all such. modifications as would be recognized by one skilled in the art are intended to be included within the scope of the following claims.

What is claimed is:

1. A medical appliance comprising:
a housing,
a door poivotably connected to the housing,
a handle mechanism arranged at the door, the handle mechanism having a handle for gripping the handle mechanism, and a part that protrudes, in the closed state of the door, into the housing,
a locking mechanism via which the door can be locked with the housing, the locking mechanism including a first part arranged at the housing and a second part arranged at the part of the handle mechanism that protrudes, in the closed state of the door, into the housing,
the first part of the locking mechanism being interlockingly engageable with the second part of the locking mechanism in the closed state of the door, such that the handle mechanism can be interlocked with the housing,
the handle mechanism allowing a user, by gripping the handle, to open and close the door in case the door is unlocked, and to move the medical appliance in case that the door is locked, and
a form fit unit that includes a form-fit element arranged at one of the handle mechanism and the housing, and a form-fit element counterpart arranged at the other of the handle mechanism and the housing, such that upon at least one of closing and locking the door, the form-fit element at least partly engages in the form-fit element counterpart,
with at least one of the form-fit element and the forms-fit element counterpart being a separate element that is mounted so as to be elastically positionable.

2. The medical appliance according to claim 1, wherein at least one of the form-fit element and the form-fit element counterpart is at least one of arranged, integrally molded, and attached at the handle mechanism.

3. The medical appliance according to claim 1, wherein at least one of the form-fit element and the form-fit element counterpart is at least one of arranged, integrally molded, and attached on a side of the housing.

4. The medical appliance according to claim 1, wherein the form-fit element is a tapered spigot and the form-fit element counterpart is a conical receptacle.

5. The medical appliance according to claim 4, wherein on closing, the handle mechanism engages in at least one of the tapered spigots elastically mounted on a side of the housing via at least one of the conical receptacles and/or the handle mechanism engages in at least one of the conical receptacles on the side of the housing via at least one of the tapered spigots elastically mounted on a side of the handle mechanism.

6. The medical appliance according to claim 4, wherein the at least one tapered spigot is pretensioned via at least one disk spring.

7. The medical appliance according to claim 4, wherein a plurality of the tapered spigots are arranged in at least two planes in the housing.

8. The medical appliance according to claim 1, wherein the locking mechanism includes a pivotable hook which cooperates with a tension bolt for locking and unlocking the door.

9. The medical appliance according to claim 1, wherein the handle mechanism is associated with the door via a secure connection.

10. The medical appliance according to claim 1, wherein the handle mechanism extends through the door in a longitudinally movable manner.

11. The medical appliance according to claim 1, wherein the handle mechanism includes at least one tension spring which can be tensioned on closing the door.

12. The medical appliance according to claim 11, further comprising a seal arranged between the door and the housing, and wherein a pressing force of the at least one tension spring is of a magnitude such that with the door closed, the seal is compressed. substantially uniformly.

13. The medical appliance according to claim 1, wherein at least a part of the housing front is formed as the door.

14. The medical appliance according to claim 13, wherein an entirety of the housing front is formed as the door.

15. The medical appliance according to claim 1, wherein the door is rotatably mounted about a lower edge thereof, with the handle mechanism being formed on an opposite side of the door.

16. The medical appliance according to claim 1, wherein the medical appliance is an apparatus for extracorporeal blood treatment.

17. The medical appliance according to claim 1, further comprising a spring element via which the at least one of the form-fit element and the form-fit element counterpart is mounted so as to be elastically positionable.

18. The medical appliance according to claim 1, wherein the at least one of the form-fit element and the form-fit element counterpart is mounted so as to be elastically positionable by a bolt extending through a bore, and a spring element.

19. The medical appliance according to claim 1, wherein the at least one of the form-fit element and the form-fit element counterpart is mounted. so as to be elastically positionable by a threaded bolt extending with a radial clearance through a bore, and is pretensioned by a spring and a nut arranged on the threaded bolt.

20. A medical appliance comprising:
a housing,
a door pivotably connected to the housing,
handle mechanism arranged at the door, the handle mechanism having a handle for gripping the handle mechanism, and a part that protrudes, in the closed state of the door, into the housing,
a locking mechanism via which the door can be locked with the housing, the locking mechanism including a first part arranged at the housing and a second part arranged at the part of the handle mechanism that protrudes, in the closed state of the door, into the housing,
the first Dart of the locking mechanism being interlockingly engageable with second part of the locking mechanism in the closed state of the door, such that the handle mechanism can be interlocked with the housing,
the handle mechanism allowing a user, by gripping the handle, to open and close the door in case the door is unlocked, and to move the medical appliance In case that the door is locked, and
a form fit unit that includes a form-fit element at one of the handle mechanism and the housing, and a form-fit element counterpart arranged at the other of the handle mechanism and the housing, such that upon at least one of closing and locking the door, the form-fit element at least partly engages in the form-fit element counterpart, with at least one of the form-fit element and the form-fit element counterpart being separate element, and
at least one spring element, via which the form-fit element can be pretensioned.

21. The medical appliance according to claim 20, wherein the spring element is and/or includes at least one of a compression, spring, a coil spring, and a disk spring, and/or wherein the spring element is at least partly formed by elastic regions of the housing.

22. The medical appliance according to claim 20, wherein the form-fit unit includes a plurality of form-fit elements and a corresponding plurality of form-fit element counterparts.

23. The medical appliance according to claim 20, wherein the form-fit element is a tapered spigot and the form-fit element counterpart is a conical receptacle.

* * * * *

UNITED STATES PATENT AND TRADEMARK OFFICE
CERTIFICATE OF CORRECTION

PATENT NO. : 9,101,703 B2
APPLICATION NO. : 13/361015
DATED : August 11, 2015
INVENTOR(S) : Jens Foerger et al.

Page 1 of 1

It is certified that error appears in the above-identified patent and that said Letters Patent is hereby corrected as shown below:

In the Specification

In column 2, line 4, the "." should be removed

In column 5, line 35, "rotatable" should read --rotatably--

In column 5, line 41, "The" should read --the--

In column 5, line 65, the "." should be removed

In the Claims

In column 6, line 28, "forms-fit" should read --form-fit--

In column 7, line 5, the "." should be removed (First Occurrence)

In column 7, line 26, the "." should be removed

In column 8, line 6, "Dart" should read --part--

In column 8, line 7, "with second" should read --with the second--

In column 8, line 12, "In" should read --in--

In column 8, line 14, "element at" should read --element arranged at--

In column 8, line 21, "being separate" should read --being a separate--

In column 8, line 26, "compression, spring" should read --compression spring--

Signed and Sealed this
Fifteenth Day of March, 2016

Michelle K. Lee
*Director of the United States Patent and Trademark Office*